United States Patent [19]
Tomes et al.

[11] Patent Number: 5,990,387
[45] Date of Patent: Nov. 23, 1999

[54] STABLE TRANSFORMATION OF PLANT CELLS

[75] Inventors: Dwight T. Tomes, Cumming; Arthur Weissinger, Des Moines, both of Iowa; John C. Sanford, Geneva, N.Y.; Theodore M. Klein, Wilmington, Del.

[73] Assignee: Pioneer Hi-Bred International, Inc., Johnston, Iowa

[21] Appl. No.: 08/319,352

[22] Filed: Oct. 6, 1994

Related U.S. Application Data

[63] Continuation of application No. 07/906,018, Jun. 26, 1992, abandoned, which is a continuation of application No. 07/711,585, Jun. 6, 1991, abandoned, which is a continuation of application No. 07/581,154, Sep. 7, 1990, abandoned, which is a continuation of application No. 07/205,155, Jun. 10, 1988, abandoned.

[51] Int. Cl.$^6$ .......................... C12N 15/00; C12N 15/82; A01H 1/06; A01H 4/00
[52] U.S. Cl. ..................... 800/293; 800/278; 800/288; 800/320.1; 800/300.1; 435/412; 435/424; 435/430; 435/430.1
[58] Field of Search .............................. 435/172.1, 172.3, 435/240.4, 320.1, 412, 424, 430, 430.1; 800/205, 320.1, 278, 288, 293, 300.1; 935/52, 53, 85

[56] References Cited

U.S. PATENT DOCUMENTS

| | | | |
|---|---|---|---|
| 4,801,545 | 1/1989 | Stuart et al. | 435/240.49 |
| 4,945,050 | 7/1990 | Sanford et al. | 435/240.4 |
| 5,350,689 | 9/1994 | Shillito et al. | 435/240.46 |
| 5,484,956 | 1/1996 | Lundquist et al. | 800/205 |
| 5,489,520 | 2/1996 | Adams et al. | 435/172.3 |
| 5,538,877 | 7/1996 | Lundquist et al. | 435/172.3 |
| 5,538,880 | 7/1996 | Lundquist et al. | 435/172.3 |
| 5,550,318 | 8/1996 | Adams et al. | 800/205 |
| 5,595,733 | 1/1997 | Carswell et al. | 424/93.21 |
| 5,770,450 | 6/1998 | Shillito et al. | 435/424 |

FOREIGN PATENT DOCUMENTS

| | | |
|---|---|---|
| 0270356 | 6/1988 | European Pat. Off. . |
| 0 290 395 | 11/1988 | European Pat. Off. . |

OTHER PUBLICATIONS

Lee 1989 (Jan.–Feb.) Plants Today, pp. 9–11.
Sanford 1990 Physiologia Plantarium 79: 206–209.
Gordon–Kamm 1991 (Jan.) In Vitro Cell Devel Biol. 27P:21–27.
Christou 1992 The Plant Journal 2(3):275–281.
Fromm et al 1986 Nature 319:791–793.
Klein et al 1988 (May) Bio/Technology 6:559–563.
Klein et al 1988 (Jun.) Proc. Nat. Acad. Sci USA 85:4305–4309.
Pouwels et al 1985 Cloning Vectors Manual. Elsevier Press Table VII–5.
Klein et al 1987 (May) Nature 327:70–73.
Weissinger et al 1987 (Mar.) I in Vitro 23(#3): 75A (Abstract 254).
Ranch et al 1985 In Vitro Cell & Devel Biol. 21: 653–658.
Hu et al 1986 In Handbook of Pl. Cell Culture; MacMillan, Evan et al (eds); vol. 4 pp. 72–74.
de la Pena et al 1987 (Jan.) Nature 325:274–276.
Journal of Cellular Biochemistry, Suppl. 13D, Mar. 27th–Apr. 7th, 1989, p. 259, abstract No. M 122, Alan R. Liss., New York, US; W. J. Gordon–Kamm et al.: "Stable Transformation of embryogenic Maize Cultures by Microprojectile Bombardment".
Theor. App. Genet., vol. 70, No. 5, 1985, pp. 505–509; D. T. Tomes, et al.: "The Effect of Parental Genotype on Initiation of Embryogenic Callus from Elite Maize (*Zea mays* L.) germplasm".
UCLA Symp. Mol. Cell. Biol., New Ser., vol. 129, 1990, pp. 21–34, Plant Gene Transfer, Proceedings of a UCLA Symposium, Park City, Utah, Apr. 1st–7th, 1989, Wiley–Liss, New York, US; J.Cao et al.: "Transformation of Rice and Maize Using the Biolistic Process".
Biotechnology, vol. 6, No. 4, Apr., 1988, pp. 397–402; I.K. Vasil: "Progress in the Regeneration and Genetic Manipulation of Cereal Crops".
Proc. Natl. Acad. Sci. USA, vol. 85, Nov. 1988, pp. 8502–8505; T. M. Klein, et al.: "Stable Genetic Transformation of Intact Nicotiana Cells by the Particle Bombardment Process".
Plant Molecular Biology, vol. 14, No. 2, Feb. 1990, pp. 261–268, Kluwer Academic Publishers, BE; D. T. Tomes, et al.: "Transgenic Tobacco Plants and Their Progeny Derived by Microprojectile Bombardment of Tobacco Leaves".
Journal of Cellular Biochemistry, Suppl. 13d, Mar. 27th–Apr. 1989, p. 268, Abstract No. M 149, Alan R. Liss, Inc. New York, US: M.C. Ross et al.: "Transient and Stable Transgenic Cells and Calli of Tobacco and Maize following microprojectile bombardment".
Proceedings of the National Academy of Sciences of the USA, vol. 86, No. 19, Oct. 1989, pp. 7500–7504, Washington, DC, US; P. Christou et al.: "Inheritance and Expression of Foreign Genes in Transgenic Soybean Plants".
Green et al. (1983) Somatic Cell Genetic Systems in Corn, *Advances in Gene Technology: Molecular Genetics of Plants and Animals*, pp. 147–157.
Rhodes et al. (1988) Genetically Transformed Maize Plants from Protoplasts, *Science*, vol. 240, pp. 204–207.

(List continued on next page.)

*Primary Examiner*—Gary Benzion
*Attorney, Agent, or Firm*—Foley & Lardner; Pioneer Hi-Bred International, Inc.

[57] ABSTRACT

The invention provides methods for producing a fertile, stably transformed, *Zea mays* plant. The methods comprise the steps of (a) providing a foreign DNA comprising an expression vector carrying a gene encoding an agronomic trait; (b) providing a maize embryogenic callus, suspension culture, or immature embryo isolated from a plant; (c) introducing the foreign DNA into the embryogenic callus, suspension culture or immature embryo isolated from a plant by one or more microparticle bombardments; and (d) regenerating fertile transgenic *Zea mays* plant.

12 Claims, 1 Drawing Sheet

OTHER PUBLICATIONS

Everett et al. (1987) Genetic Engineering of Sunflower (*Helianthus Annuus* L.), *Bio/Technology*, vol. 5, pp. 1201–1204.

Helmer et al. (1984) A New Chimeric Gene as a Marker for Plant Transformation: the Expression of *Escherichia Coli* β–Galactosidase in Sunflower and Tobacco Cells, *Bio/Technology*, pp. 520–527.

Eichholtz et al. (1987) Expression of Mouse Dihydrofolate Reductase Gene Confers Methotrexate Resistance in Transgenic Petunia Plants, *Somatic Cell and Molecular Genetics*, vol. 13(1):67–76.

De Block et al. (1984) Expression of Foreign Genes in Regenerated Plants and Their Progeny, *EMBO Journal*, vol. 3, No. 8, pp. 1681–1689.

Goldman et al., "Transformation of *Zea Mays* by *Agrobacterium Tumefaciens*", J. Cellular Biochemistry, Supplement 11B, UCLA Symposia on Molecular & Cellular Biology, (1987).

Klein et al., "Transfer of Foreign Genes Into Intact Maize Cells With High–Velocity Microprojectiles", Proc. Natl. Acad. Sci., vol. 85, pp. 305–309, (1988).

Weissinger et al., "Maize Transformation via Microprojectile Bombardment", Current Communications in Molecular Biology (1988).

Sanford et al., USDA Competitive Grant No. 86–CRCR–1–2092 (1986).

CRIS abstract of Sanford et al., USDA Competitive Grant No. 86–CRCR–1–2092 (1986).

Food and Agriculture Competitively Awarded Research and Education Grants Fiscal Year 1986 "Red Book" p. 46 (Feb. 1987).

Cover Letter and Addendum for Renewal of Sanford et al., USDA Competitive Grant No. 86–CRCR–1–2092, submitted to the USDA Mar. 5, 1987.

STABLE TRANSFORMATION OF PLANT CELLS

This is a continuation of application Ser. No. 07/906,018 filed Jun. 26, 1992, which is a continuation of application Ser. No. 07/711,585, filed Jun 6, 1991, now abandoned which was a continuation of application Ser. No. 07/581, 154, filed Sep. 7, 1990, now abandoned, which was a continuation of application Ser. No. 07/205,155, filed Jun. 10, 1988, now abandoned.

TECHNICAL FIELD

This invention relates to the use of recombinant DNA technology for the transformation of plants. More specifically, this invention concerns the techniques and materials necessary for stable transformation of plant cells and the regeneration of fertile whole plants therefrom.

BACKGROUND ART

Much research in plant molecular biology is now directed to the improvement of plant varieties via use of recombinant DNA techniques. Historically, plant breeders used classical genetic techniques to identify, preserve and crossbreed varietal lines having desirable traits. More recently, new plant varieties were induced by chemicals or by radiation treatment to mutate plant cells which were then regenerated using tissue culture techniques. These random and unpredictable approaches have obvious drawbacks. By the use of recombinant DNA technology, specific genes producing specific proteins, such as those imparting insect resistance, may be introduced into a plant to produce a desired variety with a particular trait. It is thus desirable to provide a method for regeneration of plant cells which have been transformed with recombinant DNA.

DISCLOSURE OF THE INVENTION

This invention provides methods for the construction and use of expression vectors which include at least one gene associated with the expression of a desired agronomic trait or the production of a desired protein. It further provides methods for the transformation of plant cells with the expression vector, and methods for regeneration of whole, fertile transformed plants from transformed cells in tissue culture. Finally, this invention provides transformed plants which have been produced according to the foregoing methods.

Figure 1:
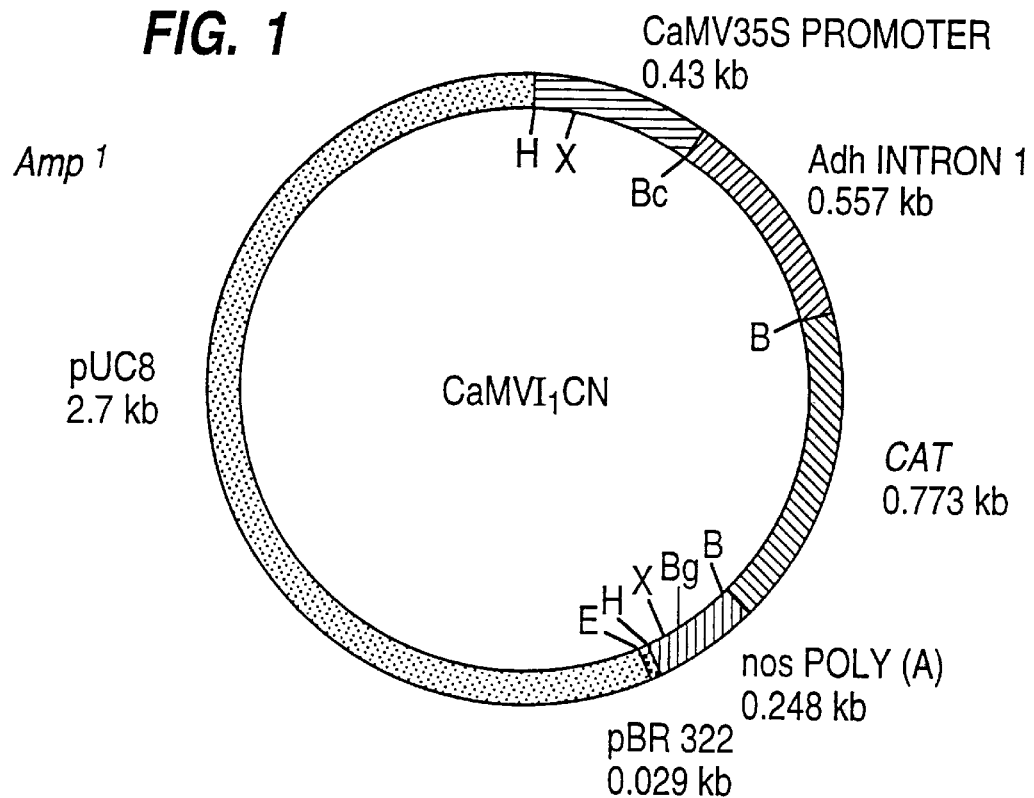
FIG. 1 is a diagram of the vector CaMVI$_1$CN showing the the DNA fragments used in the plasmid's construction.
Figure 2:
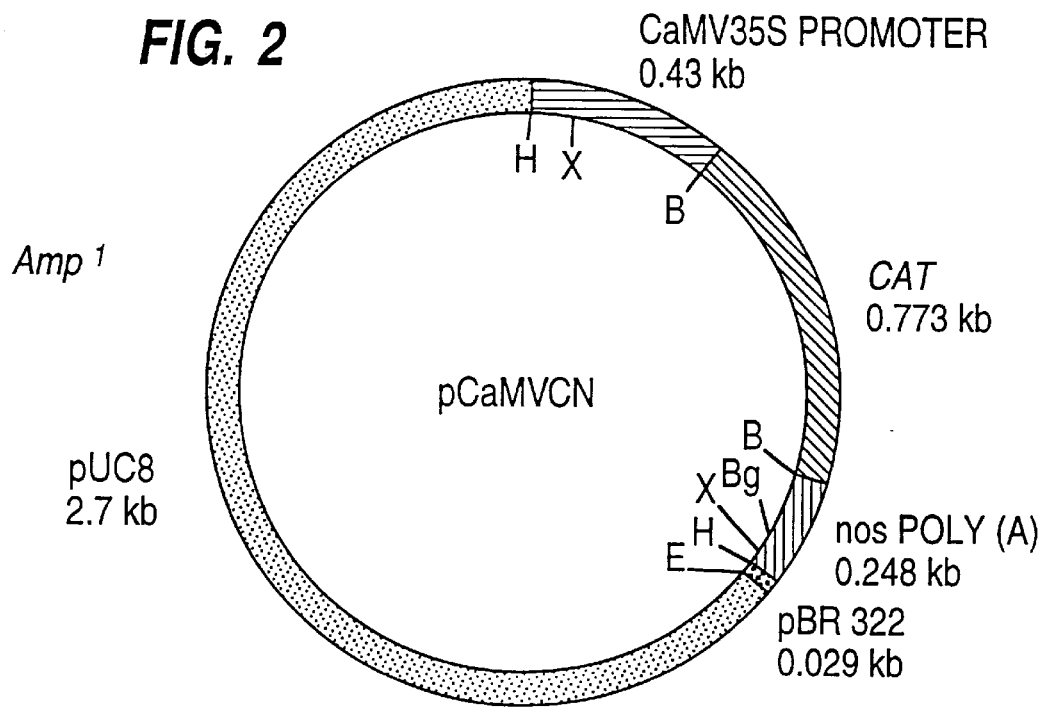
FIG. 2 is a diagram of vector pCaMVCN showing the DNA fragments used in the plasmid's construction. In the Figures the following symbols are used.

| | |
|---|---|
| B | BamHI |
| Bc | BclI |
| Bg | BglII |
| E | EcoRI |
| H | HindIII |
| X | XbaI |

DESCRIPTION OF THE PREFERRED EMBODIMENTS

This invention provides a method for transforming plant cells and regenerating the transformed cells into a whole, fertile plant, comprising the steps of inserting at least one structural gene coding for a desired trait into an expression vector;

preparing host plant cells for transformation by subculturing the cells from a parent culture of germ line cells;

introducing the vector containing the structural gene into the plant cells by one or more microparticle bombardments within a period of from about 12 hours to about 1 week after the subculture;

culturing the bombarded cells under conditions which select for survival of transformed cells; and regenerating the surviving transformed cells into a whole plant from tissue culture.

By the term "vector" herein is meant a DNA sequence which is able to replicate and express a foreign gene in a host cell. Typically, the vector has one or more endonuclease recognition sites which may be cut in a predictable fashion by use of the appropriate enzyme. Such vectors are preferably constructed to include structural gene sequences imparting antibiotic or herbicide resistance, which then serve as markers to identify and separate transformed cells. Preferred markers/selection agents include kanamycin, chlorosulfuron, hygromycin and methotrexate. A cell in which the foreign genetic material in a vector is functionally expressed has been "transformed" by the vector and is referred to as a "transformant."

A particularly preferred vector is a plasmid, by which is meant a circular double-stranded DNA molecule which is not a part of the chromosomes of the cell.

Both genomic and cDNA encoding the gene of interest may be used in this invention. The vector of interest may also be constructed partially from a cDNA clone and partially from a genomic clone. When the gene of interest has been isolated, genetic constructs are made which contain the necessary regulatory sequences to provide for efficient expression of the gene in the host cell. According to this invention, the genetic construct will contain (a) a first genetic sequence coding for the protein or trait of interest and (b) one or more regulatory sequences operably linked on either side of the structural gene of interest. Typically, the regulatory sequences will be selected from the group comprising of promoters and terminators. The regulatory sequences may be from autologous or heterologous sources.

Promoters that may be used in the genetic sequence include nos, ocs and CaMV promoters.

An efficient plant promoter that may be used as an overproducing plant promoter. Overproducing plant promoters that may be used in this invention include the promoter of the small sub-unit (ss) of the ribulose-1,5-biphosphate carboxylase from soybean (Berry-Lowe et al, *J. Molecular and App. Gen.*, 1:483–498 (1982)), and the promoter of the chlorophyll a-b binding protein. These two promoters are known to be light-induced, in eukaryotic plant cells (see, for example, *Genetic Engineering of Plants, An Agricultural Perspective*, A. Cashmore, Pelham, New York, 1983, pp. 29–38, G. Coruzzi et al., *J. Biol. Chem.*, 258:1399 (1983), and P. Dunsmuir, et al., *J. Molecular and App. Gen.*, 2:285 (1983)).

The genetic sequence comprising the gene of interest operably linked to the desired control sequences can be ligated into a suitable cloning vector. In general, plasmid or viral (bacteriophage) vectors containing replication and control sequences derived from species compatible with the host cell are used. The cloning vector will typically carry a replication origin, as well as specific genes that are capable of providing phenotypic selection markers in transformed host cells. Typically, genes conferring resistance to antibiotics or selected herbicides are used. After the genetic material is introduced into the target cells, as described below, successfully transformed cells and/or colonies of cells can be isolated by selection on the basis of these markers.

Typically, an intermediate host cell will be used in the practice of this invention to increase the copy number of the cloning vector. With an increased copy number, the vector containing the gene of interest can be isolated in significant quantities for introduction into the desired plant cells. Host cells that can be used in the practice of this invention include prokaryotes, including bacterial hosts such as *E. Coli, S. typhimurium*, and *serratia marcescens*. Eukaryotic hosts such as yeast or filamentous fungi may also be used in this invention.

The isolated cloning vector will then be introduced into the plant cell. A newly developed method of introducing genetic material into plant cells is particle gun technology, also called microprojectile or microparticle bombardment, which involves the use of high velocity accelerated particles. In this method, small, high-density particles (microprojectiles) are accelerated to high velocity in conjunction with a larger, powder-fired macroprojectile in a particle gun apparatus. The microprojectiles have sufficient momentum to penetrate plant cell walls and membranes, and can carry DNA or other substances into the interiors of bombarded cells. It has been demonstrated that such microprojectiles can enter plant cells without causing death of the cells, and that they can effectively deliver foreign genetic material into intact epidermal tissue of certain plants (Klein et al., *Nature* 327:70–73 (1987)). However, to date such techniques have not successfully been extended from large-celled model systems such as allium (onion) species to economically important species which have cells of a more typical size, nor have prior art techniques yielded fertile, mature transformed plants capable of producing genetically transformed progeny.

It has now been determined that the time within the subculture interval is an important determinant of the efficiency of stable transformation. The preferred time for microparticle bombardment is one day after subculture. When embryogenic type II callus cultures are used, several modifications of conventional techniques are required prior to their use for microparticle bombardment. During the week preceding microparticle bombardment, the cultures are transferred to fresh maintenance medium three days prior to bombardment. The callus is prepared for bombardment by passing through a 700 micron sieve which breaks the larger clumps to ones which have a maximum diameter of about 650 microns. In a further modification of callus or particle gun bombardment, sieved callus can be treated either on the same day of sieving, or alternatively from one to six days following sieving. Preferably, the cells are bombarded either on the first or second day following sieving.

In addition, it has now been determined that both sieved callus and suspension cultures require a specific density of cells per petri dish, and a specific surface area for treatment with microbombardment, if successful transformation of the cells is to be achieved. The amount of cells for treatment by microparticle bombardment will preferably range from about 2.5 mg/cm$^2$ to 10 mg/cm$^2$ of petri plate area. Most preferably, from about 5 to 10 mg/cm$^2$ will be used, lower densities being preferred where subsequent selection is to be performed, and higher densities being preferred for transient transformation analysis.

All tissues which can be cultured to give whole regenerated plants can be transformed by the present inventions so that whole plants are recovered which contain the foreign gene. When maize or sunflower are to be modified, it is preferred to use the relatively organized tissue from the immature embryo of the plant. In this method of the invention, embryos of the stage of maturity such that the apical meristem cells are readily accessible to microprojectile penetration are prepared in a method similar to that described for callus and suspension cells. In this method, the embryos are dissected from the plant approximately eight days after pollination when the embryo is just beginning to proceed from the liquid endosperm stage to the milky stage. At this stage, the embryo has an apparent coleoptile notch and only the apical meristem and perhaps the first primordia are visible. Approximately 20 embryos are placed either on filter paper or on culture medium in a manner which allows microprojectiles to penetrate the cells of the apical meristem. The apical meristem contains cells which can later give rise to either the female reproductive organs or male reproductive organs in corn, or in the case of sunflower, both male and female reproductive organs.

Some suitable plants include, for example, species from the genera Fragaria, Lotus, Medicago, Onobrychis, Trifolium, Trigonella, Vigna, Citrus, Linum, Geranium, Manicot, Daucus, Arabidopsis, Brassica, Raphanus, Sinapis, Atropa, Capsicum, Datura, Hyoscyamus, Lycopersionn, Nicotiana, Solanum, Petunia, Digitalis, Majorana, Cichorium, Helianthus, Lactuca, Bromus, Asparagus, Antirrhinum, Hemerocallis, Nemesia, Pelargonium, Panicum, Pennisetum, Ranunculus, Senecio, Salpiglossis, Cucumis, Browallia, Glycine, Lolium, Zea, Triticum, Sorghun, and Datura.

Preferred plants that are to be transformed according to the methods of this invention are cereal crops, including maize, rye, barley, wheat, sorghum, oats, millet, rice, sunflower, alfalfa, rape seed and soybean. The plant cells may be transformed with their cell walls intact, or protoplasts prepared from plant cells by known techniques can also be transformed and regenerated in the method of this invention.

Preferably, germ line cells will be used in the practice of this invention rather than somatic cells. The term "germ line cells" refers to cells in the plant organism which can trace their eventual cell lineage to either the male or female reproductive cell of the plant. Other cells, referred to as "somatic cells" are cells which give rise to leaves, roots and vascular elements which, although important to the plant, do not directly give rise to gamete cells. With regard to callus and suspension cells which have somatic embryogenesis, many or most of the cells in the culture have the potential capacity to give rise to an adult plant. If the plant originates from single cells or a small number of cells from the embryogenic callus or suspension culture, the cells in the callus and suspension can therefore be referred to as germ cells. This classification is made because these individual cells have the potential to form an entire plant, including the gamete cells. In the case of immature embryos which are prepared for treatment by microparticle bombardment, certain cells in the apical meristem region of corn have been shown to produce a cell lineage which eventually gives rise to the female and male reproductive organs. With many or most species, the apical meristem is generally regarded as giving rise to the lineage that eventually will give rise to the gamete cells. An example of a non-gamete cell in an embryo would be the first leaf primordia in corn which is destined to give rise only to the first leaf and none of the reproductive structures. Although both somatic and germ line cells can be effectively transformed for brief periods of time, up to 72 hours following microparticle bombardment, germ line cells are preferred for stable transformation which in turn results in transformed seed and their progeny.

In the overall method of this invention, a suspension of transformed plant cells containing the foreign gene is created by microparticle bombardment. Embryo formation is then induced from the cell suspension, to the stage of maturing and germination into plants. Efficient regeneration depends upon the medium, the genotype and the history of the culture. Regeneration is performed as follows:

A two-culture medium sequence is used to germinate somatic embryos observed on a callus maintenance medium. Callus is transferred first to a culture medium (maturation medium) which, instead of 0.75 mg/L, 2,4-D has 5.0 mg/L indoleacetic acid (IAA). The callus culture remains on this medium for 10 to 14 days while callus proliferation continues at a slower rate. At this culture stage, it is important that the amount of callus started on the culture medium not be too large, or fewer plants will be recovered per unit mass of material. Especially preferred is an amount of 50 milligrams of callus per plate.

Toward the end of this culture phase, observation under a dissecting microscope often indicates somatic embryos that have begun germinating although they are white in color because this culture phase is done in darkness.

Following this first culture phase, callus is transferred from "maturation" medium to a second culture medium which further promotes germination of the somatic embryos into a plantlet. This culture medium has a reduced level of indoleacetic acid versus the first culture medium, preferably a concentration of 1.0 mg/L. At this point, the cultures are placed into the light. Germinating somatic embryos are characterized by a green shoot which elongates, often with a connecting root axis. Plants are subcultured at approximately 14-day intervals until plantlet size necessitates the transfer into a culture tube instead of a petri plate. Although plants are identified rapidly, it usually takes approximately six to eight weeks to produce a plant of sufficient size for transfer to a growth chamber or greenhouse. Preferably, the plantlets will be approximately five centimeters tall with a healthy root system at the point they are transferred to a growth chamber.

Plants to be transferred to the growth chamber are removed from sterile containers and the solidified agar medium is rinsed off the roots. The plantlets are placed in a commercial potting mix in a growth chamber equipped with a misting device which maintains the relative humidity near 100% without excessively wetting the plant roots. Approximately three to four weeks are required in the misting chamber before the plants are robust enough for transplantation into pots or into field conditions. At this point, many plantlets, especially those regenerated from short-term callus cultures will grow at a rate and to a size similar to seed-derived plants. Plants regenerated from long-term callus, from suspension cultures, and from in vitro-selected callus will sometimes show phenotypic abnormalities, such as reduced plant size, leaf striping and delayed maturation. Care must be taken to assure controlled pollination with such plants. Ten to fourteen days after pollination, the plants are checked for seed set. If there is seed, the plants are then placed in a holding area in the greenhouse to mature and dry down. Harvesting is typically performed six to eight weeks after pollination.

The culture medium for initiating callus consists of a mineral salt base including major and micronutrients and vitamins (CT base) with two important additions. The first is 2,4-D at about 2 mg/L and two specific amino acids, proline at 1400 mg/L and asparagine at 900 mg/L. The preferred nutrient media employed in the regeneration of the mature plant from the transformed plant cell are described in Table A. Variations and omissions of various constituents, well known to those of ordinary skill in the plant cell culture arts, may be included or modified to accommodate species other than corn.

TABLE A

Constituents and Concentrations of Culture Medium

|  | mM | mg/l |
|---|---|---|
| Macronutrients | | |
| $KNO_3$ | 28.0 | 2,800 |
| $CaCl_2 \cdot 2H_2O$ | 2.0 | 300 |
| $MgSO_4 \cdot 7H_2O$ | 1.0 | 250 |
| $KH_2PO_4$ | 2.2 | 300 |
| $(NH_4)_2SO_4$ | 4.0 | 530 |
| $FeSO_4 \cdot 7H_2O$ | 0.11 | 37.3 |
| $Na_2 \cdot EDTA$ | 0.10 | 27.8 |
| Micronutrients | | |
| KI | 0.00045 | 0.75 |
| $H_3BO_3$ | 0.049 | 3.0 |
| $MnSO_4 \cdot H_2O$ | 0.060 | 10.0 |
| $ZNSO_4 \cdot 7H_2O$ | 0.007 | 2.0 |
| $Na_2Mo_4 \cdot H_2O$ | 0.001 | 0.25 |
| $CuSO_4 \cdot 5H_2O$ | 0.0001 | 0.025 |
| $CuCL_2 \cdot 6H_2O$ | 0.0001 | 0.025 |
| Vitamins | | |
| Nicotinic acid | 0.004 | 0.5 |
| Pyridoxine HCl | 0.002 | 0.5 |
| Thiamine HCl | 0.003 | 1.0 |
| Glydine | 0.027 | 2.0 |
| Myo-inositol | | 1,000 |
| Amino Acids | | |
| Proline | 12 | 1,400 |
| Asparagine | 6 | 900 |
| Sucrose | | 20,000 |
| Gelrite | | 3,000 |
| 2,4-D | .0038 | 0.75 |

Having now generally described this invention, the same will be better understood by reference to specific examples, which are included herein for purposes of illustration only, and are not intended to be limiting unless otherwise specified.

The plasmid $pCaMVI_1CN$ consists of the 35s promoter from cauliflower mosaic virus, a fragment (Bc to B) from the Adh1 intron 1, a CAT coding region, and the nopaline synthase polyadenylation region. This plasmid is identical to pCaMVCN with the addition of the Adh1 intron fragment Klein, T. M. et al., 1988 (June) Proc. Natl. Acad. Sci. USA 85 (4305–4309).

Separately, embryogenic suspension cultures 3-86-17 and 13-217 were derived from Type II embryogenic culture according to the method of Green et al., *Molecular Genetics of Plants and Animals*, eds. Downey et al. (Academic Press, New York, N.Y.), 20, 147 (1983). The callus was initiated from maize inbreds designated R21 (for 3-86-17) and B73× G35 (for 13-217). Inbred R21 was derived from a regenerated plant from a long-term callus culture of public inbred B73, and is very similar to B73. Both R21 and G35 are proprietary inbred lines developed by Pioneer Hi-Bred International, Inc., Des Moines, Iowa. Suspension cultures of the cultivar "Black Mexican Sweet" ("BMS") were obtained from Stanford University. The cultures were maintained in Murashige and Skoog ("MS") medium, as described in Murashige, T. and Skoog,, F., *Physiol. Plant.* 15:453–497 (1962), supplemented with 2,4- dichlorophenoxyacetic acid (2,4-D) at 2 mg/L and sucrose at 30 g/L. The suspension cultures were passed through a 710 micron sieve 7 days prior to the experiment, and the filtrate was maintained in MS medium. In preparation for microparticle bombardment, cells were harvested from the suspension culture by vacuum filtration on a Buchner funnel (Whatman #614). The same cell batch from each genotype was used within each experiment.

Prior to microparticle bombardment, 100 mg (fresh weight) of cells were placed in a 3.3 cm petri plate. The cells were dispersed in 0.5 mL fresh culture medium to form a thin layer of cells covered by a film of medium. The uncovered petri plate was placed in the sample chamber of a particle gun device manufactured by Biolistics, Inc., Geneva, N.Y. A vacuum pump was used to reduce the pressure in the chamber to 0.1 atmosphere to reduce deceleration of the microprojectiles by air friction. The cells were bombarded with tungsten particles having an average diameter of about 1.2 microns, obtained from GTE Sylvania, Precision Materials Group, Towanda, Pa. In some trials, as indicated below, cells were bombarded with microprojectiles having an average diameter of 0.6 microns (GTE Sylvania) or 2.4 microns (General Electric Corp., Refractory Metals Division, Cleveland, Ohio). The microparticles had a DNA loading applied by adding 5 uL of a 0.1 g-% solution of DNA in TE buffer at pH 7.7 to 25 uL of a suspension of 50 mg tungsten particles per mL distilled water in a 1.5 mL Eppendorf tube. In one trial, DNA from two plasmids (pCaMVI$_1$CN and pCaMVI$_1$HygN) were combined for a total of 10 uL DNA in 25 uL of tungsten particle suspension. $CaCl_2$ (25 uL of a 2.5 $\underline{M}$ solution) and spermidine free base (10 uL of a 0.1 $\underline{M}$ solution were then added to the suspension. Particles became agglomerated and settled to the bottom of the Eppendorf tube after about 10 minutes after the addition of the $CaCl_2$ and spermidine. Most of the supernatant was removed and the particles were deagglomerated by briefly touching the outside of the tube to the probe of a sonicator (Heat Systems-Ultrasonics, Inc.) Five microliters of the resulting suspension were then placed on the front surface of a cylindrical polyethylene macroprojectile. The macroprojectile was then placed into the barrel of the particle gun and a powder charge (#1 gray extra light, Speed Fasteners, Inc., St. Louis, Mo.) was loaded into the barrel behind the macroprojectile. A firing pin mechanism was used to detonate the powder charge and accelerate the macroprojectile down the barrel of the device to impact with a stopping plate. Upon impact, the momentum of the microparticles carried them from the surface of the macroprojectile, through a small aperture in the stopping plate and into the cells, which were positioned in the sample chamber 15 cm from the end of the barrel of the gun. After bombardment, the petri dish was removed from the apparatus and the cells were transferred to 5 mL fresh medium in a 15 mL polypropylene tube. The cells were then maintained in the tube with agitation at 27° C. until harvested. Control specimens were treated identically except that no DNA was applied to the tungsten particles.

In one series of trials, the plant cells were treated either with a medium of high osmotic potential or with a mixture of mineral oil and water. 100 mg of BMS cells were dispersed in 0.5 mL MS medium supplemented with mannitol (0.1 M) 30 minutes prior to bombardment. After microparticle bombardment, the cells were left in the mannitol-containing medium for an additional 30 minutes, after which the cells were resuspended in 5 mL of standard MS medium. Another sample of cells was dispersed in an emulsion of either 0.1 mL sterile mineral oil and 0.5 mL MS medium, 0.2 mL mineral oil and 0.4 mL MS medium, or in 0.6 mL MS medium lacking mineral oil. After bombardment the cells were suspended in 5 mL of MS medium.

Analyses of CAT activity were performed 12 or 96 hours After bombardment. Significantly higher levels of activity were taken to be evidence of plant cell synthesis of this foreign protein, and thus to indicate transformation of the cell. BMS, 3-86-17 and 13-217 suspension cells were collected for the assay following growth against either 10 mg/mL (BMS) or 25 mg/mL (3-86-17, 13-217) hygromycin. Tissue extracts were prepared by sedimenting the cells at approximately 13,000×G for 10 minutes in a 1.5 mL microfuge tube. The supernatant was removed and 100 uL of buffer (0.25 M Tris HCl, pH 7.8) were added to the pellet. The sample was homogenized on ice for approx. 2 minutes with a disposable polypropylene pestle driven at 300 rpm by an electric motor. After grinding, the sample was vortexed briefly to complete the extraction of soluble protein. Cell debris was removed by centrifugation at 13,000×G in a microfuge at 4° C. for 10 minutes. The supernatant was decanted and normalized to a volume of 200 uL with Tris HCl buffer.

The CAT activity in the cell extracts was determined by the procedure of Gormon et al., *Mol. Cell Biol,* 2:1044–1051 (1982) with the exception that the samples were heated at 60° C. for 12 minutes prior to the addition of substrates. The reaction mixture was incubated for 1.5 hours at 37° C., reaction products were extracted from the mixture with 300 uL of cold ethyl acetate, were air dried, and were resuspended in 20 uL of ethyl acetate for spotting on TLC plates (Bakerflex). After TLC resolution of chloramphenicol and its acetylated derivatives with chloroform:methanol (95:5), autoradiograms of the TLC plates were made (60 hr., exposure at 22° C., DuPont Cronex film).

Quantitative results were obtained by scintillation counting of separated spots of chloramphenicol and its acetylated derivatives, and the percent conversion to acetylated products was calculated. CAT activity was determined by comparison with a standard curve of acetylation conversions obtained with purified bacterial CAT. Protein in the cell extracts was determined according to Bradford, M. *Analyt. Biochem.,* 72:248–254 (1976). CAT activity was standardized on the basis of units of CAT activity per gram of soluble protein. (1 unit of CAT catalyzes acetylation of 1 ng chloramphenicol per minute at 37° C.).

CAT activity measured was compared in cell cultures of BMS following bombardment with naked microprojectiles and microprojectiles loaded with pCaMVI$_1$CN. As seen from Table 1, increases in CAT activity were consistently observed in the treatments involving the plasmid vector. The induced levels of CAT were typically 20- to 200-fold greater than the CAT levels in the controls. CAT activity in BMS was monitored over a 4-day period following bombardment. Expression of the CAT gene was detectable 24 hours after bombardment and was still high after 96 hours of incubation. CAT activity was detectable after 12 days in two embryogenic maize cell lines (3-86-17, 13-217), but not in BMS cells (Table 2). CAT activity was also measured after 96 hours in BMS cells bombarded with pCaMVCN (no intron). Expression in these cells was not greater than background levels in cells treated with uncoated microprojectiles. Consequently, all subsequent trials were performed with the pCaMVI$_1$CN plasmid.

TABLE 1

Introduction of DNA into BMS Maize Suspension Cells
Using High Velocity Microprojectiles
MEAN CAT ACTIVITY

| Experiment | N | Treatment | Control | Fold Increase | F Test |
|---|---|---|---|---|---|
| 1 | 10 | 57 (36.1) | 01 (18) | 20.1 | 0.00 (0.00) |
| 2 | 4 | 18 (19.3) | 00 (09) | 21.4 | 0.17 (0.11) |
| 3 | 3 | 43 (34.7) | 00 (02) | 173.5 | 0.10 (0.06) |
| 4 | 2 | 15 (17.1) | 00 (02) | 85.5 | 0.10 (0.26) |

Treatment and control values represent units of enzyme activity per gram of protein.
Figures in parentheses indicate % conversion of chloramphenicol to acetylated derivatives.
F Test values indicate the probability that the difference between treatment and control are due only to chance variation.

TABLE 2

Delivery of DNA into Cell Suspensions of Embryoqenic
(13-217, 3-86-17) and Non-embryogenic (BMS) Cell Lines
MEAN CAT ACTIVITY

| Cell Line | N | Treatment | N | Control | Field Increase |
|---|---|---|---|---|---|
| BMS | 2 | 00 (0.25) | 1 | 00 (0.23) | — |
| 13-217 | 2 | 02 (0.9) | — | lost | — |
| 3-86-17 | 2 | 03 (2.4) | 1 | 00 (0.44) | 5.5 |

The post-bombardment CAT activity after 96 hours of culture in embryogenic cell suspensions clearly indicated that functional DNA was being delivered into the cells, although at lower rates than observed in BMS (Table 3). Expression after 12 days tissue culture in the embryogenic cell lines was as great as at 96 hours.

TABLE 3

Delivery of DNA into Cell Suspensions of Embryogenic
(13-217, 3-86-17) and Non-embryogenic (BMS) Cell Lines
MEAN CAT ACTIVITY

| Cell Line | N | Treatment | N | Control | Field Increase |
|---|---|---|---|---|---|
| BMS | 3 | 16 (7.7) | 1 | 01 (0.5) | 15.4 |
| 13-217 | 2 | 01 (0.7) | 1 | 00 (0.3) | 2.3 |
| 3-86-17 | 2 | 02 (1.7) | 1 | 00 (0.4) | 4.3 |

EXAMPLE 2

Some samples of BMS cells were subjected to repeated bombardments with plasmid-loaded microparticles. Multiple bombardments of the same cells clearly produced levels of CAT activity than did single bombardments (Table 4). Triple bombardment was found to increase CAT activity in a similar manner in embryogenic line 3-86-17.

TABLE 4

Effect of Multiple Bombardments on BMS Using
1.2 Micron Particles Loaded with $pCaMVI_1$ CN
or Non-loaded
MEAN CAT ACTIVITY

| Bombardments | N | Treatment | N | Control | Field Increase |
|---|---|---|---|---|---|
| 1 | 4 | 35 (28.3) | 1 | 00 (0.2) | 141.5 |
| 2 | 2 | 110 (57.0) | 1 | 00 (0.2) | 285.0 |
| 3 | 2 | 135 (70.0) | 1 | 00 (0.2) | 350.0 |

EXAMPLE 3

The effect of microprojectile diameter was also determined by monitoring CAT expression after bombardment with particles of varying diameters. Significant levels of CAT activity were found only in cells bombarded with microparticles having a mean diameter of 1.2 microns; however, some clumping has been observed in particles within successfully transformed cells, so that larger particles or clumps may be used, up to about 20 microns.

TABLE 5

Effect of Microparticle Diameter on DNA Delivery
into BMS Cells, Comparing Loaded and Unloaded Particles
MEAN CAT ACTIVITY

| Size (microns) | Treatment | Control | Fold Increase |
|---|---|---|---|
| 0.6 | 00 (0.2) | 00 (0.2) | 1.0 |
| 1.2 | 15 (17.1) | 00 (0.2) | 85.8 |
| 2.4 | 00 (0.3) | 00 (0.2) | 2.5 |

EXAMPLE 4

Transformation of Regenerable Cell Line 3-86-17

An embryonic suspension culture capable of plant regeneration was obtained from the regenerative tissue culture inbred R21. This suspension was then transformed by microparticle bombardment according to the general method of Example 1. The general techniques employed were those described by Klein et al., *Proc. Nat'l Acad. Sci. USA* 85: 4305–4309 (June 1988). The cells were treated approximately one day after subculture. Clumps of suspension culture cells not greater than 710 microns were divided into 100 mg samples for bombardment. Two different vectors were used. One was the $pCaMVI_1CN$ plasmid vector containing the structural gene for chloramphenicol acetyl transferase. The second vector was a plasmid having identical regulatory sequences but containing the structural gene for beta glucuronidase. Each sample was bombarded twice with particles having a diameter of 1.2 microns and a DNA loading of 5 ug/mL.

After the bombardments, each sample was diluted with 5 mL of liquid culture medium containing 2,4-D at a concentration of 2 mg/L. Liquid medium containing the cells was transferred to 15 ml sterile centrifuge tubes where the cells were allowed to settle. Excess culture medium was removed to leave a final volume of 3 mL. Tubes with cells were incubated at 27° C. in light on a shaker at approximately 100 rpm. Cells were sampled for gene expression after 3 days. Both CAT and beta glucuronidase expression were approximately two orders of magnitude greater in the cells treated with loaded microparticles versus non-loaded controls.

EXAMPLE 5

Leaves of sterile, in vitro propagated *Nicotiana tabacum* Var. KY 17 having a length of 5 to 7 cm and a width of 2 to 3 cm were removed under aseptic conditions and prepared for microprojectile bombardment by cutting them into thin strips 1 cm long×1 mm wide in order to maximize surface area exposed to bombardment. Leaf strips were placed directly onto a culture medium consisting of MS salts and 20 mg/L naphthaleneacetic acid (NAA) and 0.5 mg/L benzylaminopyrine (BAP). 200 mg/L kanamycin was added as the selection agent. Microprojectiles were prepared by precipitating 10 ug of plasmid DNA on about 1.25 mg of tungsten particles having an average diameter of 1.2 microns. Precipitation was carried out using 0.89 M $CaCl_2$ and about 0.014 M spermidine. DNA coated particles were incorporated into cells by two consecutive bombardments in the manner previously described herein. Each bombardment delivered about 89 ug of microprojectiles.

After treatment, the strips were incubated in low light (about 350 lux) for 7 days and then transferred to fresh culture medium. Leaf pieces were transferred weekly regardless whether they showed visible growth or not. The first two subcultures were to culture medium which allowed callusing (2.0 mg/L NAA plus 0.5 mg/L BAP) followed by six successive transfers to shoot regeneration medium, which consisted of the same composition without the NAA.

Strips which were placed on culture medium without kanamycin showed rapid callus proliferation. Shoot regeneration was obvious after 5 weeks in culture. Control leaf strips placed on kanamycin-containing medium showed expansion during the first week of culture and then lost color and died over the next few weeks. Strips which had been bombarded with loaded microparticles providing the gene for kanamycin resistance at first showed symptoms of kanamycin injury. However, after two weeks in culture, very small areas of growth with differing morphology were observed. These first appeared as small protuberances at several different areas of leaf tissue. Some strips which atrophied and died left small surviving pieces of tissue. Visible callus was evident after 8 weeks' culture on medium containing 200 mg kanamycin per liter. Plant regeneration, both in the presence and absence of kanamycin, began to occur after about 10 weeks in culture.

After visible shoot initiation, plantlets were transferred to a shoot elongation/rooting medium consisting of MS salts with 4% sucrose and 50 mg/L kanamycin. About half of the plants from one of the growing calli showed shoot elongation, maintenance of green color and root elongation into the culture medium while the remainder showed poor growth characteristics, loss of greening and failure to root in the medium.

Analysis of the green healthy growing shoots showed both enzyme activity in the leaves and positive incorporation of the foreign gene into the plant cell genome as determined by both slot blot and Southern blot analysis.

The plantlets were grown to maturity and self-pollinated. Upon germination on culture medium containing 50 mg kanamycin per liter, Mendelian inheritance of the gene was established.

EXAMPLE 6

Data on Inbred Corn Line R21

The following example provides data on regeneration of inbred corn line R21, which was used in Example 4. This inbred line was obtained by recovering plants capable of seed production from a long-term callus culture (older than 12 months) of inbred B73.

TABLE 6

Tissue Culture Response - Percent Embryos Giving Rise to Type I and Type II Embryogenic Callus from TC2 Plants Regenerated from Inbred B73

| Pedigree | | 28-Day Response | |
|---|---|---|---|
| Identity | N | % Type I | % Type II |
| 710#1)**11 | 42 | 0 | 21.4 |
|  | 50 | 2.0 | 28.0 |
| B73 | 75 | 0 | 0 |
|  | 170 | 0 | 0 |

**Progenitor of R21.

TABLE 7

Percent Embryos Giving Rise to Type I and Type II Embryogenic Callus after 14 and 28 Days in Culture from Seed-Derived B73 and Several Tissue Culture Derived Plants from Inbred B73

| | | 14-Day Response | | 28-Day Response | |
|---|---|---|---|---|---|
| Pedigree | N | Type I | Type II | Type I | Type II |
| B73-TC710#1-/B73-TC694#3-)X* | 711 | 1.0 | 31.4 | 1.8 | 25.7 A |
| B73** | 279 | 0.0 | .1 | 0.0 | .6 D |

*progenitor of R21.
**5Plants from seed derived B73.

TABLE 8

Percent Embryos Giving Rise to Type I and Type II Embryogenic Callus after 14 and 28 Days in Culture from Inbred R21 Derived from B73 Callus and from Seed Derived from B73

| | | 14-Day Response | | 28-Day Response | |
|---|---|---|---|---|---|
| Pedigrees | N | Type I | Type II | Type I | Type II |
| R21* B73-TC710#1-/B73-TC694#5)2X | 80 | 3.8 B | 3.8 D | 0.0 | 6.3 |
| B73 | 277 | 0.0 B | 0.0 B | 0.0 | 0.0 |

*Data shown from same ears used for per se and top cross yield data.

TABLE 9

Plant Regeneration from R21 and B73 Embryogenic Cultures Approximately 28 Days after Culture Initiation

| Genotype | Number Embryos | X Plants/Embryo |
|---|---|---|
| R21 | 14 | 2.85 |
| B73 | 2 | 2.50 |
| B73 Regenerate | 1 | 1.00 |

What is claimed is:

1. A method of producing a fertile, stably transformed *Zea mays* plant, comprising the steps of:
   (a) providing a foreign DNA comprising an expression vector carrying a gene of interest;
   (b) providing a *Zea mays* embryogenic callus;

(c) introducing the foreign DNA into the embryogenic callus by one or more microparticle bombardments; and (d) regenerating the fertile *Zea mays* plant which is stably transformed with the foreign DNA.

2. The method according to claim 1, wherein the embryogenic callus is Type I callus.

3. The method according to claim 1, wherein the embryogenic callus is Type II callus.

4. The method according to claim 1, wherein the gene is a herbicide resistance gene.

5. The method according to claim 1, wherein step (b) further comprises providing the *Zea mays* embryogenic callus on a solid suport.

6. The method according to claim 1, wherein step (b) further comprises providing the *Zea mays* embryogenic callus on a liquid medium.

7. The method according to claim 4, wherein the herbicide resistance gene is a chlorsulfuron resistance gene.

8. A method of producing a fertile, stably transformed *Zea mays* plant, comprising the steps of:

(a) providing a foreign DNA comprising an expression vector carrying a gene of interest;

(b) providing a *Zea mays* embryogenic suspension culture;

(c) introducing the foreign DNA into the embryogenic suspension culture by one or more microparticle bombardments; and (d) regenerating the fertile *Zea mays* plant which is stably transformed with the foreign DNA.

9. The method according to claim 8, wherein the gene is a herbicide resistance gene.

10. The method according to claim 9, wherein the herbicide resistance gene is a chlorsulfuron resistance gene.

11. The method according to claim 8, wherein step (b) further comprises providing the *Zea mays* embryogenic suspension culture on a solid suport.

12. The method according to claim 8, wherein step (b) further comprises providing the *Zea mays* embryogenic suspension culture on a liquid medium.

* * * * *